United States Patent
Walther et al.

(10) Patent No.: US 8,814,887 B2
(45) Date of Patent: Aug. 26, 2014

(54) SURGICAL IMPLANT

(75) Inventors: Christoph Walther, Kattendorf (DE);
Barbara Schuldt-Hempe, Bad Bramstedt (DE)

(73) Assignee: Ethicon, Inc., Somerville, NJ (US)

( * ) Notice: Subject to any disclaimer, the term of this patent is extended or adjusted under 35 U.S.C. 154(b) by 1092 days.

(21) Appl. No.: 11/817,086

(22) PCT Filed: Feb. 23, 2006

(86) PCT No.: PCT/EP2006/001654
§ 371 (c)(1),
(2), (4) Date: Sep. 16, 2008

(87) PCT Pub. No.: WO2006/092236
PCT Pub. Date: Sep. 8, 2006

(65) Prior Publication Data
US 2009/0069826 A1    Mar. 12, 2009

(30) Foreign Application Priority Data
Mar. 1, 2005   (DE) .................. 10 2005 009 356

(51) Int. Cl.
*A61B 17/08* (2006.01)
*A61F 2/00* (2006.01)

(52) U.S. Cl.
CPC .................. *A61F 2/0063* (2013.01)
USPC ...................... 606/151; 623/11.11; 623/23.72

(58) Field of Classification Search
USPC .............................. 623/11.11, 23.72; 606/151
See application file for complete search history.

(56) References Cited

U.S. PATENT DOCUMENTS

| 4,572,174 | A | | 2/1986 | Eilender |
| 5,368,602 | A | | 11/1994 | De la Torre |
| 5,700,583 | A | * | 12/1997 | Jamiolkowski et al. ...... 428/482 |
| 6,162,962 | A | | 12/2000 | Hinsch et al. |
| 6,171,318 | B1 | * | 1/2001 | Kugel et al. .................. 606/151 |
| 6,224,616 | B1 | | 5/2001 | Kugel |
| 6,241,768 | B1 | | 6/2001 | Agarwal |
| 6,258,124 | B1 | | 7/2001 | Darois et al. |
| 6,319,264 | B1 | * | 11/2001 | Tormala et al. ............... 606/151 |
| 6,669,735 | B1 | | 12/2003 | Pelissier |
| 2003/0078602 | A1 | | 4/2003 | Rousseau |

FOREIGN PATENT DOCUMENTS

| DE | 19613730 C2 | 8/2002 |
| DE | 10155842 A1 | 5/2003 |
| DE | 10353930 A1 | 11/2003 |
| DE | 10355189 A1 | 11/2003 |
| EP | 0898944 B1 | 3/1999 |
| FR | 2857851 A1 | 7/2003 |
| JP | 2004-508134 A1 | 3/2004 |

(Continued)

OTHER PUBLICATIONS

U. Klinge et al.: Pathophysiologie de Bauchdecken [Pathophysiology of the abdominal wall], Der Chirurg (1196) 67: 229-233.

*Primary Examiner* — Gregory Anderson
(74) *Attorney, Agent, or Firm* — E. Richard Skula

(57) ABSTRACT

A surgical implant has a mesh-like base structure (2) and a film (4). The film (4) extends over at least part of the base structure (2), is connected to the base structure (2) in partial regions, and has a coefficient of kinetic friction, relative to rat skin, of not more than 0.25. The film (4) is preferably absorbable.

17 Claims, 2 Drawing Sheets

(56) References Cited

FOREIGN PATENT DOCUMENTS

Figure 1:
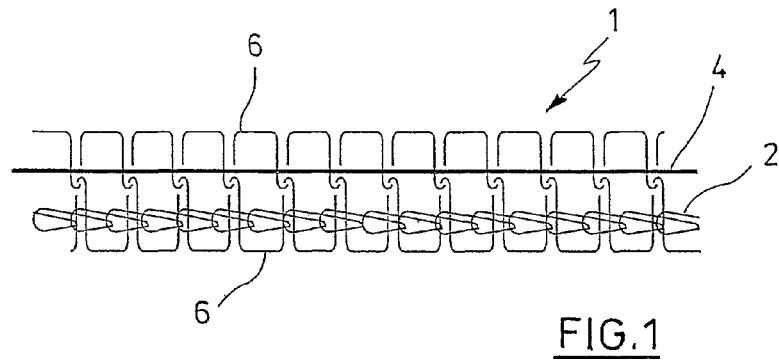

| WO | WO9951163 A1 | 10/1999 |
| WO | WO 02/087468 A1 | 11/2002 |
| WO | WO 03/041613 A1 | 5/2003 |
| WO | WO 2004/012627 A1 | 2/2004 |
| WO | WO 2005/051448 A1 | 6/2005 |

* cited by examiner

SURGICAL IMPLANT

CROSS REFERENCE TO RELATED APPLICATION

This application is the national stage of Application No. PCT/EP2006/001654, filed 23 Feb. 2006, which application claims priority from DE 10 2005 009 356.6, filed 1 Mar. 2005, which are all incorporated by reference herein in their entireties.

The invention relates to a surgical implant which, for example, can be used to repair inguinal hernias.

EP 0 898 944 A2 discloses a hernia implant in which a two-layer base is positioned in the preperitoneal space beneath the hernial orifice by means of a deployment device. A channel issuing from the base extends through the hernial orifice and is provided with a collar at its end. A disadvantage here is that the base does not always reliably deploy inside the preperitoneal space and its edge may become folded or get stuck. Moreover, the base remains relatively rigid.

US 20030078602 A1 discloses a two-layer hernia implant in which one layer is absorbable and the other layer is not absorbable.

DE 196 13 730 A1 describes an areal implant for strengthening or closure of body tissue, in which implant an absorbable film can be applied as a temporary stiffening material to one or both sides of a mesh-like base structure.

DE 101 55 842 A1 discloses an areal implant with a mesh-like base structure which is stable over a long period of time, has pores measuring in the range of 1.5 mm to 8 mm and is provided, at least in a partial region, with a synthetic and absorbable polymer film on both sides. The two polymer films are bonded or welded to one another in the pores of the base structure.

Areal implants comprising a film permit only poor growth of tissue through them, because the applied film constitutes a barrier. If the film is absorbable, this disadvantageous effect is present at least temporarily.

WO 2004/012627 A1 discloses a hernia implant with a retention structure which constitutes an aid for deployment and stabilizing of the implant. This implant comprises two stiff, superposed meshes, with small pores, made of polypropylene, a sewn-on membrane made of e-PTFE, and a reinforcement ring made of polyethylene terephthalate in a sewn channel inside the polypropylene mesh pouch.

A disadvantage of this is that the polypropylene mesh pouch represents a large amount of material, is stiff and adapts only poorly to the anatomical circumstances, which leads to an excessive foreign-body reaction with formation of a scar plate. Moreover, the microporous membrane made of e-PTFE is not incorporated in the tissue but instead is enclosed by a tissue capsule; adhesion is avoided.

U.S. Pat. No. 6,224,616 B1 discloses a hernia implant with two mesh-like layers between which a pouch is formed. The pouch contains a spring structure which opens the implant out in one plane. The edge of this implant may fold up or over during use, which is a disadvantage.

A further hernia implant is known from U.S. Pat. No. 6,669,735 B1. Here, an absorbable ring is secured on the periphery of a non-absorbable mesh, which ring is bendable but resumes its original shape after deformation.

U.S. Pat. No. 5,368,602 A discloses a flexible surgical mesh with at least one elongate, semi-rigid element which constitutes an aid for insertion of the implant. The semi-rigid elements can be formed integrally with the mesh or as separate components.

There are, in principle, disadvantages in deploying an implant mesh in the preperitoneal space by means of an absorbable or non-absorbable spreader ring or similar application aids (for example nitinol wires or spring wires).

Thus, it is reported that the ring can break, entailing the risk of perforation of the intestine. When, in the course of normal wound healing, the tissue grows into the mesh, a scar forms and leads to wound contraction. The mesh into which the tissue has grown is thereby also contracted, but the spreader ring does not take part in this contraction. This can cause a three-dimensional deformation of the mesh, and the deformed mesh can then no longer perform the function of closing the hernia.

It is an object of the invention to make available a surgical implant which is suitable in particular for hernia repair, can easily deploy in the intraperitoneal space, for example, permits good growth of tissue through it during the entire healing process and does not later lead to complications.

This object is achieved by a surgical implant having the features of Claim 1. Advantageous embodiments of the invention are set out in the dependent claims.

The surgical implant according to the invention has a mesh-like base structure and a film which extends over at least part of the base structure. The film is connected to the base structure in partial regions of the film. The film is preferably absorbable. The coefficient of kinetic friction between film and rat skin is not more than 0.25. This figure relates to dry (i.e. not pre-moistened) film. A test procedure for determining the coefficients of kinetic friction and also the corresponding coefficients of static friction is explained in detail further below.

The coefficient of kinetic friction between film and rat skin can be within any range whose lower limit is greater than 0 and smaller than the upper limit, and whose upper limit is not more than 0.25; all possible numerical values for this are herewith considered as having been disclosed.

When the implant according to the invention or parts thereof which have the abovementioned features are introduced into the preperitoneal space, the disadvantages outlined above in relation to the previously known implants do not occur. The implant is fitted in such a way that, after placement in the preperitoneal space, the side with the mesh-like base structure points towards the transversalis fascia (i.e. outwards) and the film side points towards the peritoneum (i.e. the intestinal side). By virtue of the film, the implant provides sufficient initial stiffness for reliable deployment in the preperitoneal space, but, in the case of an absorbable film, the implant parts in the preperitoneal space are sufficiently soft after a few days or within a few weeks, and good incorporation of body tissue is also permitted. Moreover, deployment is facilitated by the relatively low friction between the film and the body tissue. After absorption of the film, an areal implant structure with good tissue incorporation and of greatly reduced stiffness is left within the preperitoneal space.

Reliable deployment or spreading-out is also ensured without a spreader ring or similar, that is to say the edge configuration of the implant does not endanger the patient. The film, at least on part of the edge of the base structure, preferably reaches at least as far as the edge of the base structure and optionally even extends beyond the edge of the base structure. In this way, an edge is obtained which is easily palpable and has an atraumatic configuration. It is of advantage if the film extends beyond the edge of the base structure, because then, during application, the mesh webs at the ends do not catch so easily in the body tissue. If the film is connected to the base structure at least on part of the edge of the base structure (and preferably about the entire circumference of the base structure), the edge of the base structure cannot fold or bend over. These features make handling the implant much easier.

According to the invention, the film is not connected to the mesh-like base structure across the entire surface, but only in partial regions, e.g. at points and/or in the edge area.

Therefore, the mesh side can be reliably incorporated into the fascia structures, since sufficient hollow spaces are present between film and mesh-like base structure, and the base structure can adapt well to the contour of the body tissue lying over it. Within the first hours and days of wound-healing, fibrin is admitted, not just on one side, but so as to enclose the mesh webs, with the result that, in this early phase of wound-healing, the base structure and the implant are held in a stable position by means of processes taking place in the body. In this way, it is also possible to achieve fixation of the implant, for example by means of rapidly absorbable suture material, as a result of which disadvantages can be avoided, for example in inguinal hernia repair. This is because implants in inguinal hernia repair are usually fixed with non-absorbable suture material, for example polypropylene, which in isolated cases can lead to chronic pain and to irritation of the nerves.

As has already been mentioned, the film ensures reliable deployment of the implant. The properties of the film in this respect can be adjusted, for example via its material, stiffness or thickness or the nature of the preliminary treatment (e.g. stretching). In preferred embodiments, the film has a thickness in the range of 0.01 mm to 3 mm, preferably in the range of 0.025 mm to 1 mm, and its bending modulus of elasticity is less than 2500 N/mm$^2$. Special configuration of the edge is not needed, because the film has sufficient stiffness.

The film greatly reduces the friction relative to the underlying body tissue, while the mesh-like base structure has a higher coefficient of kinetic friction or of static friction relative to the tissue and bears closely on the overlying tissue. A test procedure for determining coefficients of friction of mesh structures and films relative to animal tissue is described further below. The results show that the friction of meshes is typically at least twice as high as the friction of selected films relative to body tissue.

In preferred embodiments, the difference in the coefficients of kinetic friction of the film in the dry state and in the wet state is less than 0.2, preferably less than 0.1. This distinguishes the film from, for example, collagen-coated materials which, in the moist state, have considerably lower coefficients of friction than in the dry state, as will be explained further below in the example.

The film can be connected to the base structure in different ways, e.g. sewn on, embroidered, or bonded on (including by thermal means) in partial regions (e.g. in points or along lines or strips, such as the peripheral edge) or welded thermally. The welding techniques here also include, in the wider sense, thermal deformation of the film (below the melting point of the film). A connection between film and base structure is conceivable in the edge area, for example, but also in areal patterns or, for example, as an arrow shape. The data for the coefficients of friction relate to the film as such, without friction-increasing effects, e.g. embroidered patterns.

The preferred connection techniques are embroidering or sewing, since the implants are predominantly sterilized by ethylene oxide sterilization. The reason is that, in the case of adhesively bonded points or melted-on points, it is not possible to reliably avoid possible microorganisms becoming trapped in these adhesion points or melt points, in the production process, and thus not being killed off by the sterile gas.

Examples of embroidered patterns or sewn patterns are given further below. An embroidered edge can also be configured so that it is palpable, which can facilitate handling of the implant. The implant can also have embroidered structures designed as reinforcements, e.g. rib-like structures.

The implant according to the invention can be formed as an areal structure, e.g. by consisting only of a mesh-like structure with film. However, the implant can also be formed as a three-dimensional structure, e.g. by having a mesh-like base structure with film and also additional structures which are of three-dimensional configuration. An expansion into the third dimension can also be achieved with an inherently areal structure (that is to say, for example, a mesh-like base structure with film) which is curved and, if appropriate, stabilized in its shape.

In an advantageous embodiment, the implant has two wings extending across one another and spaced apart from one another, at least one of said wings having a mesh-like base structure and a film with the features discussed above. The two wings can in this case be connected by a cylinder-like structure designed for insertion into a hernial orifice. Such implants are suitable for treatment of hernias, in particular if the implant is intended to cover a hernial gap in the preperitoneal space. The wing configure according to the invention in this case comes to lie in the preperitoneal space, as has been explained above, and the other wing is fitted above this one, into the body tissue. Implants of comparable geometry are sold by Ethicon under the name "PHS" (Prolene Hernia System), see also EP 0 898 944 B1. Other geometries for three-dimensional implants according to the invention are also conceivable.

The film can be provided with one or more perforations, for example, in the "PHS" geometry, with a central opening (e.g. 18 mm diameter), in order to permit better placement in the preperitoneal space.

Examples for the material of the mesh-like base structure are polymers of alpha-olefins (including fluorine-containing alpha-olefins), e.g. polypropylene, polyvinylidene fluoride, aliphatic polyesters (e.g. of glycolic acid or lactic acid), aromatic polyesters (e.g. polyethylene terephthalate), and also copolymers or mixtures thereof. Particularly suitable examples are mixtures of polyvinylidene fluoride and copolymers of vinylidene fluoride and hexafluoropropylene, sold by Ethicon under the name "Pronova". Partially absorbable mesh structures are also advantageous; suitable examples of these are structures with "Vicryl" (Polyglactin 910, copolymer of glycolide and lactide in the ratio 90:10, Ethicon) and polypropylene, structures with "Monocryl" (Polyglecaprone 25, copolymer of glycolide and $\epsilon$-caprolactone, Ethicon) and "Pronova" or preferably structures with "Monocryl" and polypropylene. Aliphatic polyesters or polyether esters are especially suitable for the absorbable component.

The base structure can have a multifilament mesh, a monofilament mesh, or also a mesh configured as a mix of monofilaments and multifilaments. The elasticity behaviour of the base structure can be adapted in the manner described in DE 196 13 730 A1. Meshes with small pores or meshes with monofilament reinforcements are likewise conceivable.

The mesh-like base structure can also be coated, for example metal-coated (with titanium or zirconium or other metals). Coatings are also suitable which receive active substances (drug carriers) that are released after implantation. Examples of additives are internal plasticizers (e.g. citrates), or active substances such as triclosan, which can be incorporated into the base structure, for example by the method described in DE 103 55 189 A1.

The film preferably contains polymers and/or copolymers of lactides, glycolides, caprolactone, trimethylene carbonate, polyhydroxybutyrate and/or polyhydroxyvalerate. Other advantageous materials are poly-p-dioxanone (PDS) and polyoxaester. As a constituent of the implant according to the invention, the film also has coefficients of friction within the required range. In a given film, the coefficient of friction also depends, inter alia, on the method of production of the film, which also determines the surface properties. The question of whether a given film has a coefficient of friction within the required range, and is therefore suitable for the implant according to the invention, can be easily ascertained by a skilled person carrying out specific tests.

Complete or partial colouring of the implant facilitates its orientation during the operation.

As has been explained, the surgical implant according to the invention is especially suitable for hernia repair, particularly if the implant is intended to cover a hernial gap in the preperitoneal space. However, if the film is additionally equipped with anti-adhesion means (e.g. coated with ORC or collagen) or if it is made of polyoxaester or is coated with polyoxaester, this implant can also be fitted in the intraperitoneal space.

Figure 2:
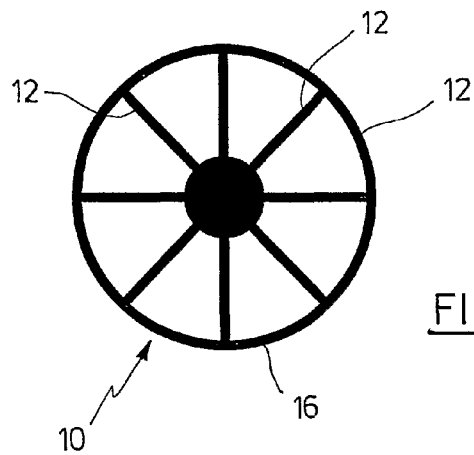
Figure 3:
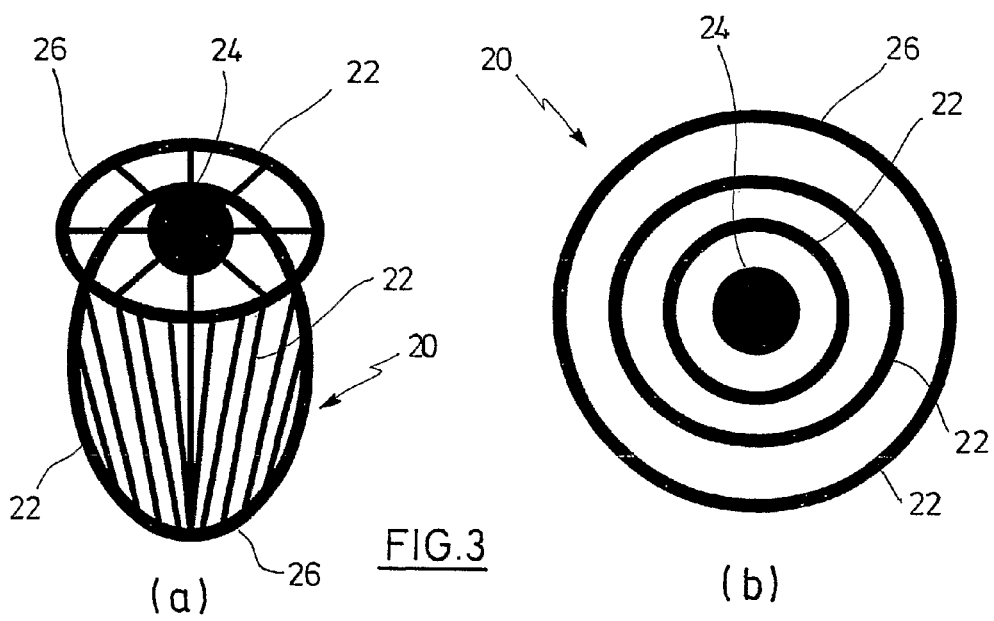
Figure 3:
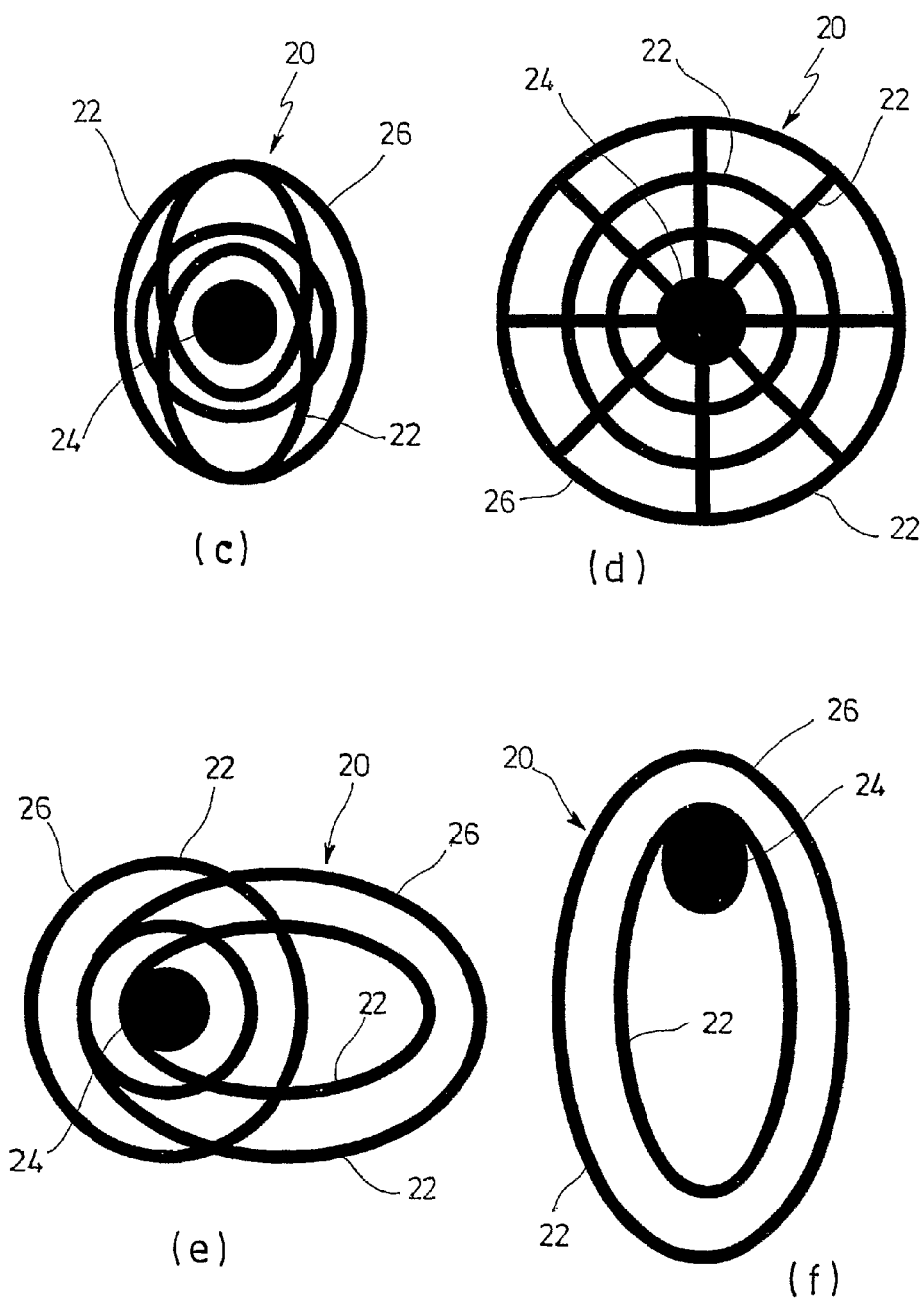

The invention is described in more detail below with reference to examples. In the drawings:

FIG. 1 shows a diagrammatic longitudinal section through a region of an implant according to the invention, with a mesh-like base structure and a film, FIG. 2 shows a diagrammatic plan view of an embodiment of the implant according to the invention, and FIG. 3 shows, in parts (a) to (f), various embodiments of a wing, configured according to the invention, of a two-winged hernial implant, in diagrammatic plan views.

EXAMPLES OF GEOMETRIC SHAPES

FIG. 1 shows a diagrammatic longitudinal section through a region of a surgical implant 1. The implant 1 has a mesh-like base structure 2, e.g. crochet galloon, and a film 4 which, in the illustrative embodiment, is absorbable. The film 4 is connected to the base structure 2 by a seam 6 in partial regions of the base structure 2; the longitudinal section according to FIG. 1 extends through such a partial region. In the illustrative embodiment, the seam 6 is a double saddle stitch seam.

FIG. 2 shows a diagrammatic plan view of an embodiment of the implant, designated by 10. The dark lines 12 (zones) are the partial regions in which the film is connected to the base structure, e.g. by seams or embroidering. A partial region of this kind runs along the periphery of the base structure and extends as far as the edge 16 of the base structure. The film is therefore securely connected to the base structure in the edge area of the base structure. The film itself can also extend beyond the edge 16, but this is not shown in FIG. 2.

In FIG. 3, six embodiments for a lower wing 20 (base) of a two-winged hernia implant are shown in parts (a) to (f) in diagrammatic plan views. A hernia implant of this kind has a further wing (collar) which runs at a distance from the base 20 and is connected to the base 20 via a cylindrical structure. The underlying geometrical principle ("PHS" geometry) of such a hernia implant is described in EP 0 898 944 A2. The base 20 is configured according to the invention. For simplicity, the same reference numbers are used in parts (a) to (f) of FIG. 3. The base 20 is constructed similarly to the implant 10 according to FIG. 1 and has a base structure and a film which is connected to the base structure in the dark, linear zones 22, e.g. by sewing, embroidering, gluing or welding. The circular area 24 marks the site of application of the aforementioned cylindrical structure. In the illustrative embodiments, one of the zones 22 runs along the edge 26 of the base structure, but the film can also extend beyond the edge 26.

As can be seen from parts (a) to (f) in FIG. 3, the zones 22 can also serve to reinforce the structure, e.g. in the form of radially extending or circular reinforcements.

Other Examples of Embodiments

Table 1 below shows summarized examples of embodiments and material combinations, specifically for two-winged surgical implants with the "PHS" geometry for treatment of hernias (see above). In these implants, the wing (underlay) configured according to the invention is fitted in the preperitoneal space and the other wing (overlay) is fitted above this; both wings are linked by a connector which comes to lie in the hernial orifice.

The material designations here, and in the rest of the text, are as follows:

PP: Polypropylene (sold by Ethicon under the name "Prolene")
Vicryl: Polyglactin 910, copolymer of glycolide and lactide in the ratio 90:10 (Ethicon)
Monocryl: Polyglecaprone 25, copolymer of glycolide and ε-caprolactone (Ethicon)
Pronova: Mixture of polyvinylidene fluoride and copolymer of vinylidene fluoride and hexafluoropropylene (Ethicon)
PDS: Poly-p-dioxanone
"Vicryl", "Monocryl" and "Pronova" are trade names of Ethicon.

TABLE 1

| Overlay with connector | Underlay | | | | |
| --- | --- | --- | --- | --- | --- |
|  | Mesh | Film | Shape | Embroidered edge | Embroidery yarn |
| PP | PP/Monocryl | Monocryl | Round | Only at edge | Absorbable |
| PP/Vicryl | PP/Vicryl | Polydioxanone | Oval | Several at uniform spacing | Non-absorbable |
| PP/Monocryl | Pronova | Thickness: 50 μm | Ellipse |  | Monofilament |
| Pronova | Pronova/ Monocryl | Thickness: Preferably 200 μm | With central perforation |  | Multifilament |
| Pronova/ Monocryl |  | Thicknesses: 50 to 500 μm |  |  | Coloured or uncoloured |

The bending modulus of elasticity of films can be measured in a three-point bending test (e.g. distance of the bearings 20 mm, crosshead speed 25 mm/min). For "Monocryl" films of different thicknesses, this gives ca. 450 N/mm².

In the illustrative embodiments, the films used in the implants or implant parts configured according to the invention are absorbable. "Monocryl" has a breaking-strength loss (measured after incubation in a phosphate buffer at 37° C.) of less than 10% of the original breaking strength within ca. 3 to 20 days. A likewise suitable film of PDS has a corresponding breaking-strength loss after ca. 10 to 50 days.

Examples of Bonding

The film can be connected to the mesh-like structure with the aid of a second film by means of thermal bonding. It must be ensured that the bonding of the two films to one another and to the mesh takes place under sterile conditions.

In one example of this, a "Monocryl" film was bonded to an "Ultrapro" mesh (base structure; "Ultrapro": implant mesh sold by Ethicon with polypropylene and "Monocryl"), specifically by means of an intermediate layer (second film) arranged in partial regions of the "Monocryl" film and made of a thin "PDS" film. In the example, the "PDS" film was melted on at 130° C. in order to serve as an adhesive film between the "Monocryl" film (melting point ca. 190° C.) and the "Ultrapro" mesh (melting point ca. 165° C.).

Determination of the Coefficients of Friction

The coefficients of friction (coefficient of kinetic friction and coefficient of static friction) of the film were measured relative to rat skin, using a rat model, since the results are easy to reproduce, and rat tissue is easily obtainable.

For this purpose, a test specimen with the film to be examined is placed flat on a metal plate. Freshly prepared rat skin is placed, free from folds, on a square cork board (slide) so that the superficial fascia is pointing outwards. The square cork board with the rat skin (contact surface between test specimen and the superficial fascia of the rat ca. 10×10 cm) is loaded with a defined weight (pressing force) and pulled over the test specimen at a test speed of 200 mm/min with a tension testing machine (flexible wire, one end secured on the cork board, the second end on the load cell of the tension testing machine, the wire guided round low-friction rollers). The static friction and kinetic friction forces are determined from the resulting force-distance diagram, and from this it is possible to calculate a coefficient of static friction and a coefficient of kinetic friction (as quotient of the frictional force and pressing force exerted by the tension testing machine).

In the tests carried out, the selected pressing force and the contact surface resulted in a contact pressure of ca. 730 Pa (5.5 mmHg), which corresponds to low intra-abdominal pressures. (In the tension-free state, the intra-abdominal pressure is between 200 Pa (1.5 mmHg) and 800 Pa (6 mmHg; U. Klinge et al.: Pathophysiologie der Bauchdecken [Pathophysiology of the abdominal wall], Der Chirurg (1196) 67: 229-233). A doubling of the contact pressure to ca. 1730 Pa (13 mmHg) led directly proportionally to a doubling of the frictional forces, while the coefficients of friction in the examined pressure range (up to about 2200 Pa or 16.5 mmHg) remained almost unchanged, that is to say are to be seen as "matter constants".

Results of Friction Measurements

According to measurements carried out using the model explained above (rat model), the kinetic friction force of commercially available meshes is in the order of 5N, whereas a "Monocryl" film, for example, has kinetic friction forces of less than 1 N.

In contrast to collagen film, for example, the frictional force of "Monocryl" film is not appreciably influenced by surrounding fluids. The comparison values for collagen film are ca. 3.5 N (dry) and ca. 0.5 N (wet), measured on the collagen film side of the "Parietex" mesh implant from Sofradim; in coatings with "Interceed" (oxidized regenerated cellulose), there are similar differences between the dry and the wet state.

Meshes or implants fitted in the dry state and coated on one side with collagen film, or meshes fitted in the dry state and coated with "Interceed", have the disadvantage that they deploy poorly in the preperitoneal space and are difficult to position since, on the one hand, the mesh webs get caught and, on the other hand, the much higher coefficient of friction makes deployment on the peritoneal layer difficult.

Table 2 shows the measurement results in detail for different samples compared to commercially available standard implants. The samples designated by 1 and 2 are the films of implants according to the invention, while the other samples are conventional implants.

The coefficients of static friction and of kinetic friction of films of the implant according to the invention are ca. 0.03 to ca. 0.20 for the dry state and the wet state and are much lower in comparison to conventional implant meshes. The differences between the measurements in the wet state and in the dry state are less than 0.1. By contrast, collagen film for example (as constituent of the "Parietex" mesh implant from Sofradim, a spacer knit with collagen film; sample 3) shows coefficients of friction of ca. 0.6 (static friction) and 0.34 (kinetic friction) in the dry state, while, in the wet state, the collagen film has a coefficient of friction of ca. 0.06 to 0.07. Implants which are not moistened and are coated on one side with collagen film deploy only poorly in the preperitoneal space. These differences between wet and dry are even more pronounced, for example, in implants which are coated with ORC (oxidized regenerated cellulose; trade name, e.g. "Interceed"; sample 4), for example the "Proceed" implant (sample 5), or which contain ORC. The coefficients of kinetic friction and of static friction in the dry state are greater than 1 and decrease markedly in the wet state, depending on the amount of water taken up.

The coefficients of friction of commercially available implants of polypropylene ("Prolene"; sample 6) are lower in the dry state and higher in the moist state and are of the order of above 0.25 to ca. 0.7 for static friction and above 0.15 to ca. 0.5 for kinetic friction. A mesh with large pores such as "Vypro II" (Ethicon; sample 7), comprising a polypropylene component and an aliphatic polyester ("Vicryl"), tends to have higher coefficients of friction than a pure polypropylene mesh. The "Vypro" mesh (Ethicon; sample 8) also contains polypropylene and "Vicryl". Another large-pore mesh with an absorbable component ("Monocryl") and a non-absorbable component of polypropylene is the "Ultrapro" mesh (Ethicon; sample 9).

TABLE 2

| Sample | Material | Measurement state | | Force applied [N] | Frictional force [N] | | Coefficient of friction | |
|---|---|---|---|---|---|---|---|---|
| | | wet | dry | | Static friction | Kinetic friction | Static friction | Kinetic friction |
| 1 | "Monocryl" film | | x | 7.62 | 0.39 | 0.34 | 0.05 | 0.04 |
| | | | x | 7.62 | 0.29 | 0.24 | 0.04 | 0.03 |
| | | | x | 7.62 | 0.52 | 0.40 | 0.07 | 0.05 |
| | | x | | 7.62 | 0.33 | 0.24 | 0.04 | 0.03 |
| 2 | PDS film | 100 μm | x | 7.62 | 0.43 | 0.41 | 0.06 | 0.05 |
| | | 250 μm | | x | 7.62 | 1.43 | 0.45 | 0.19 | 0.06 |
| | | 250 μm | x | | 7.62 | 0.10 | 0.50 | 0.10 | 0.07 |
| 3 | "Parietex" mesh | Knit side | | x | 7.67 | 7.05 | 6.80 | 0.92 | 0.89 |
| | | | | x | 7.67 | 7.88 | 7.70 | 1.03 | 1.00 |
| | | Film side | | x | 7.67 | 4.56 | 2.60 | 0.59 | 0.34 |
| | | | x | | 7.67 | 0.52 | 0.45 | 0.07 | 0.06 |
| 4 | "Interceed" | Front | | x | 7.62 | 12.00 | 12.00 | 1.57 | 1.57 |
| | | | x | | 7.62 | 10.09 | 9.50 | 1.32 | 1.25 |
| 5 | "Proceed" | "Interceed" side | | x | 7.62 | 9.60 | 9.00 | 1.26 | 1.18 |
| | | | | x | 7.62 | 18.86 | 12.00 | 2.48 | 1.57 |
| 6 | "Prolene" mesh (5 mil = 0.127 mm "Prolene" lengthwise) | Front | | x | 7.49 | 2.82 | 1.40 | 0.38 | 0.19 |
| | | | | x | 7.49 | 1.99 | 1.15 | 0.27 | 0.15 |
| | | | x | | 7.49 | 5.08 | 4.60 | 0.68 | 0.61 |
| | | | x | | 7.49 | 4.67 | 4.20 | 0.62 | 0.56 |
| | "Prolene" | Back | | x | 7.49 | 2.52 | 2.00 | 0.34 | 0.27 |
| | | | | x | 7.49 | 2.99 | 2.60 | 0.40 | 0.35 |
| | | | | x | 7.49 | 2.79 | 2.35 | 0.37 | 0.31 |
| | | | | x | 7.49 | 3.20 | 2.60 | 0.43 | 0.35 |
| | | | | x | 7.49 | 2.69 | 2.10 | 0.36 | 0.28 |
| | "Prolene" mesh (5 mil = 0.127 mm "Prolene" crosswise) | Front | | x | 7.49 | 2.18 | 2.50 | 0.29 | 0.33 |
| | | | x | | 7.49 | 2.85 | 2.20 | 0.38 | 0.29 |
| | | | x | | 7.49 | 3.50 | 2.00 | 0.47 | 0.27 |
| | | Back | | x | 7.49 | 3.06 | 1.90 | 0.41 | 0.25 |
| | | | | x | 7.49 | 3.14 | 1.85 | 0.42 | 0.25 |
| | | | x | | 7.49 | 4.20 | 3.60 | 0.56 | 0.48 |
| | | | x | | 7.49 | 4.70 | 3.65 | 0.63 | 0.49 |
| 7 | "Vypro II" | Lengthwise | x | | 7.21 | 6.59 | 5.80 | 0.91 | 0.80 |
| | | | x | | 7.21 | 5.95 | 5.80 | 0.83 | 0.80 |
| | | | x | | 7.21 | 5.87 | 5.60 | 0.81 | 0.78 |
| | | | x | | 7.21 | 6.14 | 5.60 | 0.85 | 0.78 |
| | | | | x | 7.21 | 4.26 | 4.10 | 0.59 | 0.57 |
| | | | | x | 7.21 | 4.48 | 4.10 | 0.62 | 0.57 |
| | | | | x | 7.21 | 4.24 | 4.10 | 0.59 | 0.57 |
| | | | | x | 7.21 | 4.50 | 4.10 | 0.62 | 0.57 |
| 8 | "Vypro" | Lengthwise | | x | 14.42 | 8.89 | 8.00 | 0.62 | 0.55 |
| | | | | x | 21.63 | 14.84 | 14.00 | 0.69 | 0.65 |
| 9 | "Ultrapro" | | | x | 7.21 | 5.24 | 5.10 | 0.73 | 0.71 |
| | | | | x | 7.21 | 5.33 | 5.10 | 0.74 | 0.71 |
| | | | | x | 7.21 | 5.43 | 5.00 | 0.75 | 0.69 |

The invention claimed is:

1. A surgical implant comprised of a mesh base and a bioabsorbable film, which film extends over at least part of the mesh base structure, is connected to the mesh base structure in partial regions, and has a coefficient of kinetic friction in the dry state, relative to rat skin, of not more than 0.25, and wherein the difference between the coefficient of friction in the dry state and the coefficient of friction in a wet state is less than 0.2, and wherein the implant is deployable in a patient into a preperitoneal space to repair a tissue defect in a dry state, and wherein the implant has sufficient initial stiffness in the dry state for effective deployment in the preperitoneal space.

2. The implant according to claim 1, characterized in that the film is absorbable.

3. The implant according to claim 1, characterized in that the film, at least on part of an edge of the mesh base structure, reaches at least as far as the edge of the mesh base structure and optionally extends beyond the edge of the base structure.

4. The implant according to claim 1, characterized in that the film is connected to the mesh base structure at least on part of an edge of the mesh base structure.

5. The implant according to claim 1, characterized in that the film is connected to the mesh base structure in at least one of the following ways comprised of: sewn on, embroidered, glued on in partial regions, or welded on in partial regions.

6. The implant according to claim 1, characterized in that the implant has embroidered structures designed as reinforcements.

7. The implant according to claim 1, characterized in that the film has a thickness in the range of 0.01 mm to 3 mm.

8. The implant according to claim 1, characterized in that the film has a bending modulus of elasticity of less than 2500 N/mm$^2$.

9. The implant according to claim 1, characterized in that the difference in the coefficients of kinetic friction of the film in the dry state and in the wet state is less than 0.2.

10. The implant according to claim 1, characterized in that the implant is formed as an areal structure.

11. The implant according to claim 1, characterized in that the implant is formed as a three-dimensional structure.

12. The implant according to claim 1, characterized in that the implant has two wings extending across one another and spaced apart from one another, at least one of said wings having a mesh base structure and a film with the features according to claim 1.

13. The implant according to claim 12, characterized in that the two wings are connected by a cylinder-like structure designed for insertion into a hernial orifice.

14. The implant according to claim 1, characterized in that the mesh base structure is comprised of at least one of the materials selected from the group consisting of polypropylene, polyvinylidene-fluoride, polymers of alpha-olefins, polymers of fluorine-containing alpha-olefins, mixtures of-21-polyvinylidene fluoride and copolymers of vinylidene fluoride and hexafluoropropylene, aliphatic polyesters, aliphatic polyesters of glycolic acid, aliphatic polyesters of lactic acid, copolymers of glycolide and lactide, copolymers of glycolide and 8-caprolactone, aromatic polyesters, polyethylene terephthalate, and polyether ester.

15. The implant according to claim 1, characterized in that the film is comprised of at least one of the materials selected from the group consisting of polymers and copolymers of lactides, glycolides, caprolactone, trimethylene carbonate, polyhydroxybutyrate, polyhydroxyvalerate, poly-p-dioxanone, and polyoxaester.

16. The implant according to claim 1, characterized in that the mesh base structure is comprised of at least one of the elements selected from the group consisting of monofilaments, multifilaments, coatings, coatings with metal, coatings with titanium, coatings with zirconium, coatings configured as medicament supports, internal plasticizers, citrates as internal plasticizers, active substances, and triclosan as active substance.

17. The implant according to claim 1, characterized in that the film has at least one perforation.

* * * * *